(12) United States Patent
Williams et al.

(10) Patent No.: US 10,342,534 B2
(45) Date of Patent: Jul. 9, 2019

(54) SURGICAL STAPLING DEVICE WITH RELEASABLE KNIFE CARRIER

(71) Applicant: Covidien LP, Mansfield, MA (US)

(72) Inventors: Justin Williams, Southbury, CT (US); Joseph Guerrera, Watertown, CT (US); David Valentine, East Hampton, CT (US)

(73) Assignee: Covidien LP, Mansfield, MA (US)

( * ) Notice: Subject to any disclaimer, the term of this patent is extended or adjusted under 35 U.S.C. 154(b) by 278 days.

(21) Appl. No.: 15/467,153

(22) Filed: Mar. 23, 2017

(65) Prior Publication Data

US 2018/0271524 A1     Sep. 27, 2018

(51) Int. Cl.
*A61B 17/072* (2006.01)
*A61B 17/068* (2006.01)
(Continued)

(52) U.S. Cl.
CPC .......... *A61B 17/072* (2013.01); *A61B 17/068* (2013.01); *A61B 17/07207* (2013.01);
(Continued)

(58) Field of Classification Search
CPC ................ A61B 17/068; A61B 17/072; A61B 17/07207; A61B 17/115; A61B 17/1114;
(Continued)

(56) References Cited

U.S. PATENT DOCUMENTS

| 3,193,165 A | 7/1965 | Akhalaya et al. |
| 3,388,847 A | 6/1968 | Kasulin et al. |

(Continued)

FOREIGN PATENT DOCUMENTS

| CA | 908529 A | 8/1972 |
| CA | 2805365 A1 | 8/2013 |

(Continued)

OTHER PUBLICATIONS

U.S. Appl. No. 15/343,995, filed Nov. 4, 2016, inventor Joseph Guerrera.

(Continued)

*Primary Examiner* — Scott A Smith

(57) ABSTRACT

A surgical stapling device includes reload assembly that is supported on a distal portion of an elongate shaft of the surgical stapling device. The reload includes a housing, a pusher assembly movably supported within the housing, a knife carrier movably supported within the pusher assembly, and an annular knife supported on the knife carrier. The elongate body includes a pusher drive member and a knife carrier pusher. The knife carrier includes first engagement structure that is configured to releasably engage second engagement structure formed on the knife carrier pusher to releasably couple the knife carrier pusher to the knife carrier. The knife carrier supports at least one detent that is movable into contact with a distal portion of the pusher drive member as the knife carrier is retracted to urge the first engagement structure out of engagement with the second engagement structure to uncouple the knife carrier from the knife carrier pusher.

19 Claims, 9 Drawing Sheets

(51) Int. Cl.
 A61B 17/115 (2006.01)
 A61B 17/29 (2006.01)
 A61B 17/00 (2006.01)
(52) U.S. Cl.
 CPC . *A61B 17/1155* (2013.01); *A61B 2017/00473* (2013.01); *A61B 2017/00477* (2013.01); *A61B 2017/07214* (2013.01); *A61B 2017/07257* (2013.01); *A61B 2017/07271* (2013.01); *A61B 2017/07278* (2013.01); *A61B 2017/07285* (2013.01); *A61B 2017/2931* (2013.01)
(58) Field of Classification Search
 CPC ...... A61B 17/1155; A61B 2017/07214; A61B 2017/07271; A61B 2017/07285; A61B 2017/07257; A61B 2017/00473; A61B 2017/00477
 USPC .. 227/19, 175.1, 175.2, 176.1, 178.1, 180.1; 606/139, 153, 219
 See application file for complete search history.

(56) References Cited

U.S. PATENT DOCUMENTS

| | | | |
|---|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |

(56) References Cited

U.S. PATENT DOCUMENTS

| | | |
|---|---|---|
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |

(56) References Cited

U.S. PATENT DOCUMENTS

| | | |
|---|---|---|
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2004/0217146 A1* | 11/2004 | Beck ................ A61B 17/115 227/176.1 |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0108740 A1* | 5/2010 | Pastorelli ............ A61B 17/1114 227/178.1 |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |

(56) References Cited

U.S. PATENT DOCUMENTS

| | | |
|---|---|---|
| 2011/0011916 A1 | 1/2011 | Levine |
| 2011/0024481 A1* | 2/2011 | Bettuchi .............. A61B 17/072 |
| | | 227/180.1 |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0147435 A1* | 6/2011 | Heinrich .......... A61B 17/00491 |
| | | 227/180.1 |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0007999 A1 | 1/2016 | Latimer et al. |
| 2018/0125495 A1 | 5/2018 | Sgroi, Jr. |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3108828 A2 | 12/2016 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013-138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2004112618 A2 | 12/2004 |
| WO | 2008/107918 A1 | 9/2008 |
| WO | 2017172704 A2 | 10/2017 |

OTHER PUBLICATIONS

U.S. Appl. No. 62/417,537, filed Nov. 4, 2016, inventor Anthony Sgroi, Jr.
European Search Report dated Aug. 14, 2018 in EP 18163304.

* cited by examiner

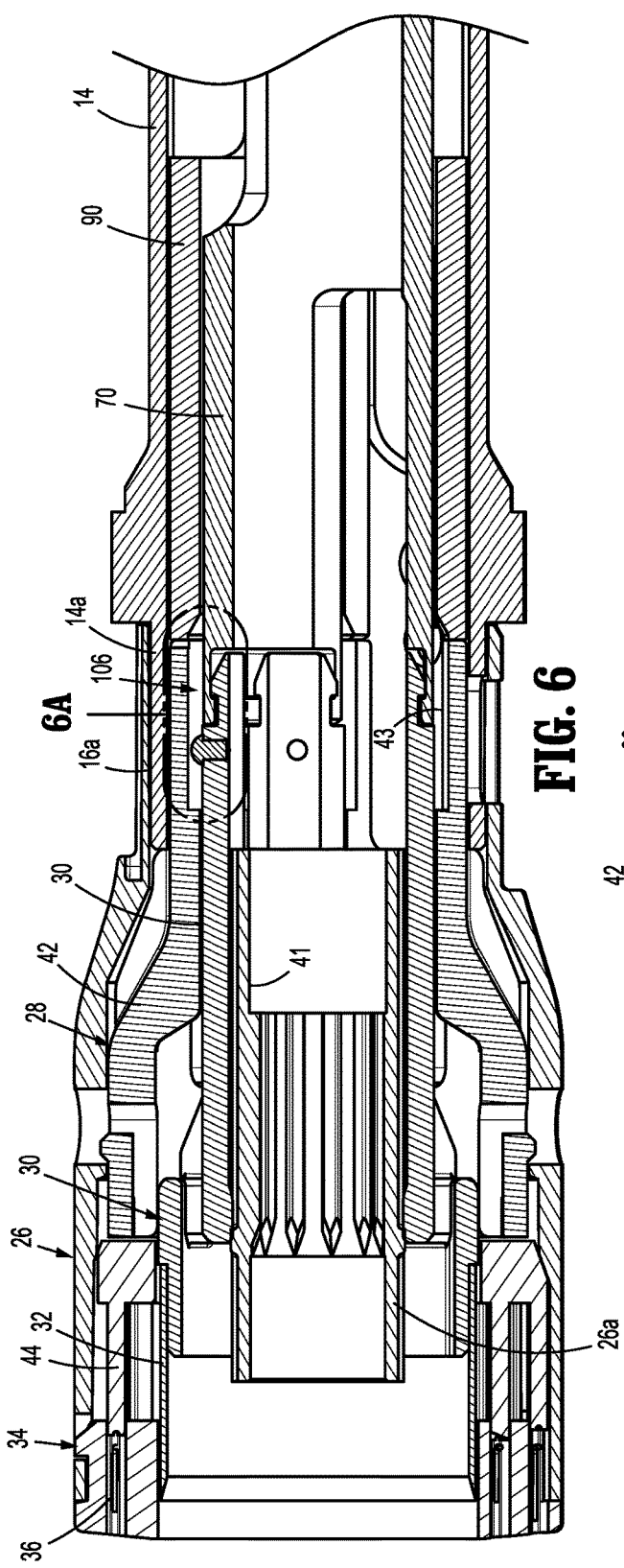
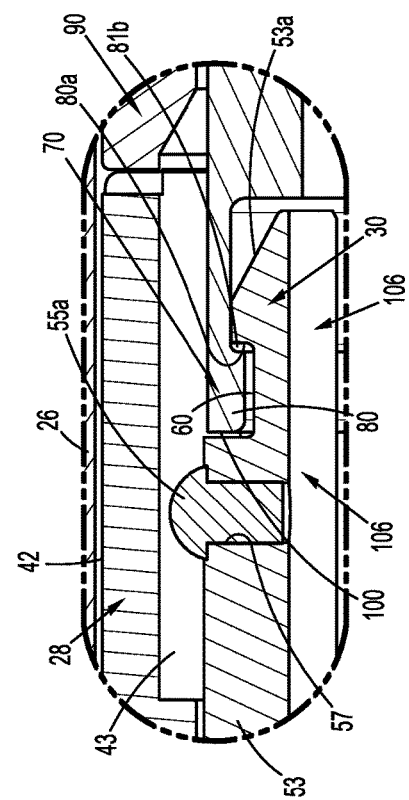
FIG. 6
FIG. 6A

SURGICAL STAPLING DEVICE WITH RELEASABLE KNIFE CARRIER

BACKGROUND

1. Technical Description

The present disclosure is directed to surgical stapling devices and, more particularly, to surgical stapling devices that include a knife carrier that is releasably coupled to a knife carrier pusher.

2. Background of Related Art

Conventional circular stapling devices include an elongate body and a shell or reload assembly supported on a distal portion of the elongate body. The reload assembly includes a staple cartridge that supports a plurality of staples, a pusher that is movable in relation to the staple cartridge to eject staples from the staple cartridge, a knife, and a knife carrier that supports the knife and is movable through the staple cartridge to core tissue. The surgical stapling device also includes a pusher drive member and a knife carrier pusher that are supported within the elongate body. The pusher drive member is engaged with the staple pusher and is movable to move the staple pusher to eject staples from the staple cartridge. Similarly, the knife carrier pusher is engaged with the knife carrier and is movable to effect movement of the knife carrier to core tissue. In some circular stapling devices, the knife carrier pusher and the knife carrier are separable to facilitate separation of the reload assembly from the elongate body of the surgical stapling device.

In some designs, a back angle may be formed on the knife carrier pusher to facilitate separation of the knife carrier pusher from the knife carrier. In these designs, if the back angle selected is too small, the knife carrier can be damaged upon removal of the reload from the elongate body, and if the back angle selected is too large, disengagement of the knife carrier pusher from the knife carrier can occur prematurely such that full retraction of the knife is not achieved.

A need exists in the stapling arts for a simple but reliable mechanism to effect engagement and disengagement of the knife carrier and the knife carrier pusher at the appropriate times.

SUMMARY

In one aspect of the disclosure, a surgical stapling device includes an elongate body defining a longitudinal axis and having a proximal portion and a distal portion, and a reload assembly. The elongate body includes a pusher drive member and a knife carrier pusher. The pusher drive member has an inner surface defining a through bore having a tapered distal portion. The reload assembly includes a housing, a staple cartridge supporting a plurality of staples, and a pusher assembly movably supported within the housing between a retracted position and an advanced position to eject the plurality of staples from the staple cartridge. The pusher assembly has an inner surface defining a through bore. The inner surface has a proximal portion defining a counter bore. The reload assembly also includes a knife carrier supporting a knife. The knife carrier includes first engagement structure and at least one detent. The knife carrier pusher includes second engagement structure configured to releasably engage the first engagement structure of the knife carrier to couple the knife carrier pusher to the knife carrier. The first engagement structure is movable from a first position engaged with the second engagement structure to a second position disengaged from the second engagement structure. When the stapling device is in a pre-fired state, the at least one detent is positioned within the counter bore of the pusher assembly, and when the knife carrier is retracted after the stapling device has been actuated to eject the plurality of staples and to cut tissue, the detents are positioned to engage the tapered distal portion of the pusher drive member to urge the first engagement structure from the first position towards the second position to uncouple the knife carrier from the knife carrier pusher.

In embodiments, the knife carrier includes a proximal portion defined by a plurality of flexible legs.

In some embodiments, the at least one detent includes a detent supported on each of the plurality of flexible legs.

In certain embodiments, each of the detents extends outwardly from a longitudinal axis of the knife carrier.

In embodiments, the knife carrier is movably positioned within the through bore defined by the pusher assembly.

In some embodiments, each of the detents is integrally formed with a respective one of the plurality of flexible legs.

In certain embodiments, the first engagement structure is formed on the proximal portion of the plurality of flexible legs.

In embodiments, the first engagement structure includes a recess formed on the proximal portion of the plurality of flexible legs.

In some embodiments, the recess includes an annular channel.

In certain embodiments, the proximal portion of each of the plurality of flexible legs is tapered towards a longitudinal axis of the knife carrier in the proximal direction.

In embodiments, the second engagement structure includes a protrusion configured to be received within the recess of the first engagement structure.

In some embodiments, the protrusion is annular.

In certain embodiments, the recess of the first engagement structure is defined by a proximal wall that is orthogonal in relation to the longitudinal axis of the knife carrier.

In embodiments, the protrusion of the second engagement structure is defined by a proximal wall which is orthogonal in relation to the longitudinal axis of the knife carrier pusher.

In some embodiments, the proximal wall of the second engagement structure is positioned to engage the proximal wall of the first engagement structure to translate proximal movement of the knife carrier pusher into proximal movement of the knife carrier.

In certain embodiments, the handle assembly is an electrically powered handle assembly.

In embodiments, the reload assembly is releasably coupled to the elongate body.

In some embodiments, the pusher assembly includes an annular pusher and a staple pushing member.

In certain embodiments, the annular pusher is positioned to abut a proximal portion of the staple pushing member.

BRIEF DESCRIPTION OF THE DRAWINGS

Various embodiments of the presently disclosed surgical stapling device including a releasable knife carrier are described herein below with reference to the drawings, wherein:

FIG. 6 is a cross-sectional view taken along section line 6-6 of FIG. 2 illustrating the distal portion of the surgical stapling device in a pre-fired state;

FIG. 6A is an enlarged view of the indicated area of detail shown in FIG. 6;

DETAILED DESCRIPTION OF EMBODIMENTS

Figure 1:
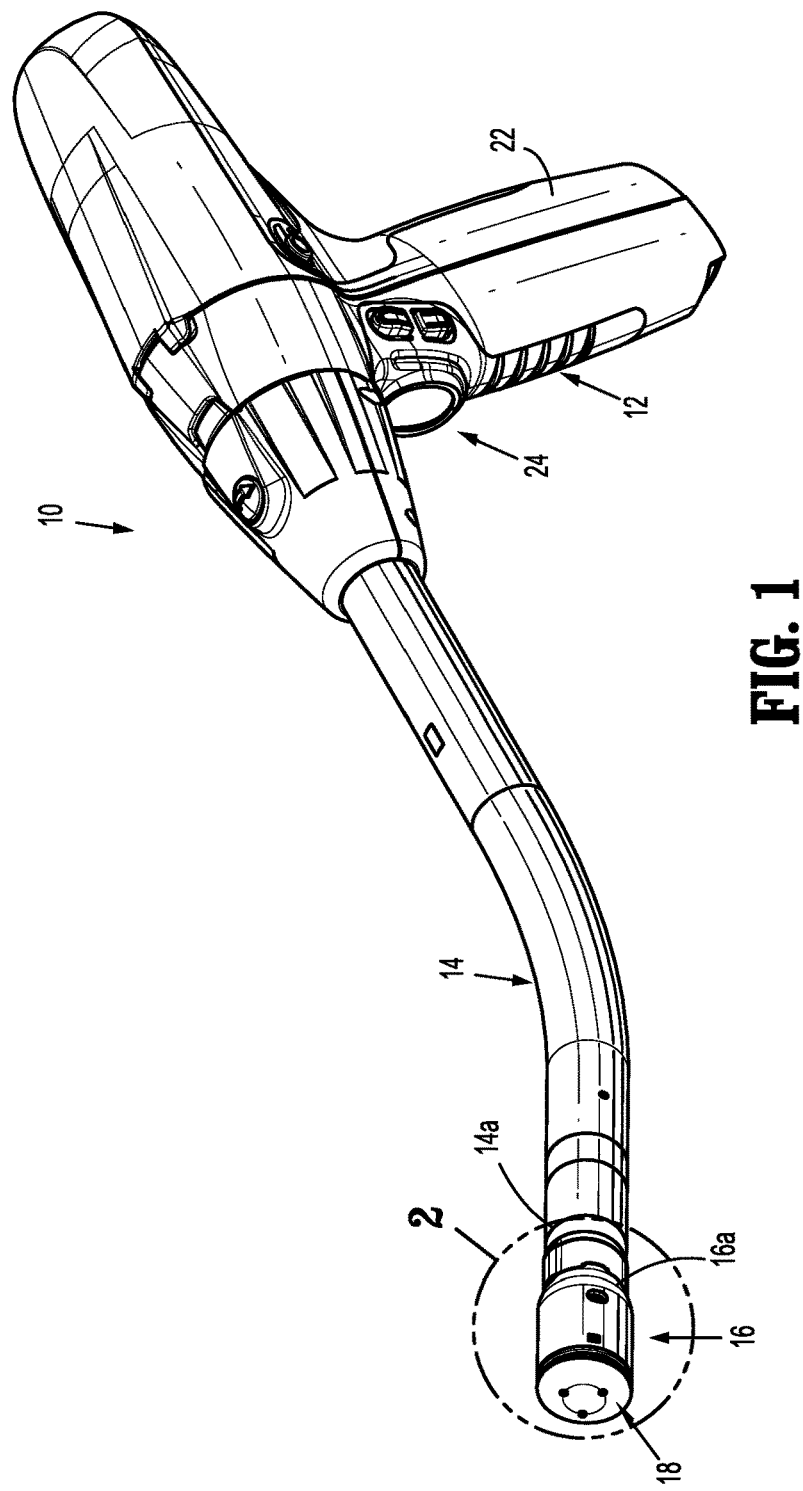
FIG. 1 is a side perspective view of one exemplary embodiment of the presently disclosed surgical stapling device including a reload assembly and an anvil assembly with the anvil assembly in an approximated position.

The presently disclosed circular stapling device will now be described in detail with reference to the drawings in which like reference numerals designate identical or corresponding elements in each of the several views. In this description, the term "proximal" is used generally to refer to that portion of the stapling device that is closer to a clinician, while the term "distal" is used generally to refer to that portion of the stapling device that is farther from the clinician.

The presently disclosed circular stapling device includes a shell or reload assembly that is supported on a distal portion of an elongate shaft of the stapling device. The reload assembly includes a housing, a staple cartridge that supports a plurality of annular rows of staples, a staple pusher assembly, a knife carrier, and an annular knife supported on the knife carrier. The pusher assembly includes an inner surface defining a through bore. The inner surface of the pusher assembly has a proximal portion that defines a counter bore. The knife carrier is movably positioned within the through bore of the pusher assembly.

The elongate body includes a pusher drive member and a knife carrier pusher. The pusher drive member has an inner surface that defines a through bore that is aligned with the through bore of the pusher assembly. A distal portion of the inner surface of the pusher drive member is tapered outwardly in a distal direction. The knife carrier is movably positioned within the pusher assembly and pusher drive member and includes a plurality of proximally extending resilient legs that are movable from a first position engaged with the knife carrier pusher to couple the knife carrier with the knife carrier pusher to a second position disengaged from the knife carrier pusher. Each of the resilient legs supports an outwardly extending detent that is positioned within the counter bore of the pusher assembly when the stapling device is in a pre-fired state. When the stapling device is actuated to fire staples, the pusher drive member is advanced to advance the pusher assembly to eject staples from the staple cartridge. Thereafter, the knife carrier pusher is advanced to advance the knife carrier and the knife to cut or core tissue. After tissue is stapled and cored, the pusher drive member is retracted, and the knife carrier pusher is subsequently retracted to retract the knife carrier and the knife into the housing. As the knife carrier is retracted, the detents on the resilient legs of the knife carrier are moved from a position within the counter bore of the pusher assembly into contact with the tapered distal portion of the pusher drive member to urge the resilient legs of the knife carrier to the second position to uncouple the knife carrier pusher from the knife carrier. The presently disclosed reload assembly minimizes the likelihood of premature disengagement of the knife carrier from the knife carrier pusher while reducing the force required to effect uncoupling of the knife carrier from the knife carrier pusher after the knife has been fully retracted into the housing.

Figure 2:
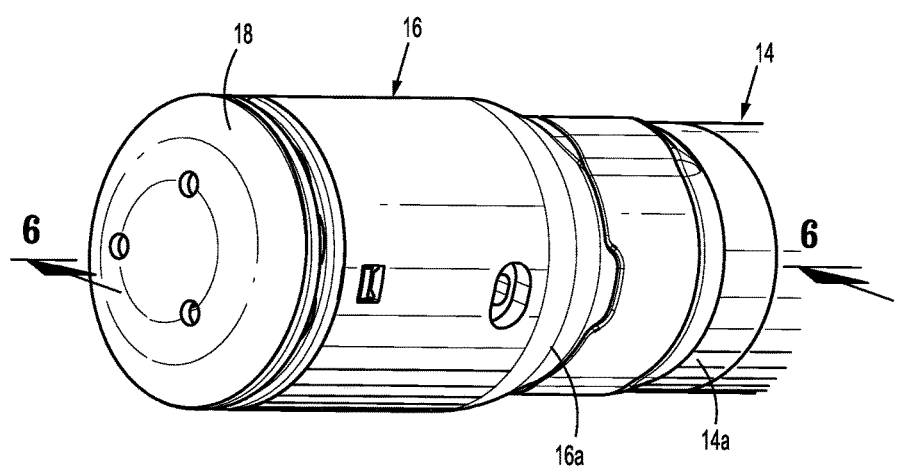
FIG. 2 is an enlarged view of the indicated area of detail shown in FIG. 1.

FIGS. 1 and 2 illustrate an exemplary embodiment of the presently disclosed surgical stapling device 10. The surgical stapling device 10 includes a handle assembly 12, an elongate body or adaptor assembly 14, a reload assembly 16, and an anvil assembly 18 supported for movement in relation to the reload assembly 16 between spaced and approximated positions as is known in the art. The reload assembly 16 includes a proximal portion 16a that is releasably coupled to a distal portion 14a of the elongate body 14. The handle assembly 12 includes a stationary grip 22, and actuation buttons 24 for controlling operation of the various functions of the surgical stapling device 10 including approximation of the reload and anvil assemblies 16, 18, firing of staples 36 from the reload 16, and cutting or coring of tissue. Although the surgical stapling device 10 is illustrated as an electrically powered stapling device including an electrically powered handle assembly 12 and an elongate body 14 in the form of an adaptor assembly that translates power from the handle assembly 12 to the reload and anvil assemblies 16, 18, it is envisioned that the present disclosure could also be incorporated into a manually powered stapling device. Examples of electrically powered stapling devices can be found in U.S. Pat. No. 9,023,014 ("the '014 patent"), and U.S. Pat. No. 9,055,943 ("the '943 patent) which are incorporated herein by reference in their entirety. Alternately, the surgical stapling device 10 can be configured for use with a robotic system and need not include a handle assembly.

Figure 3:
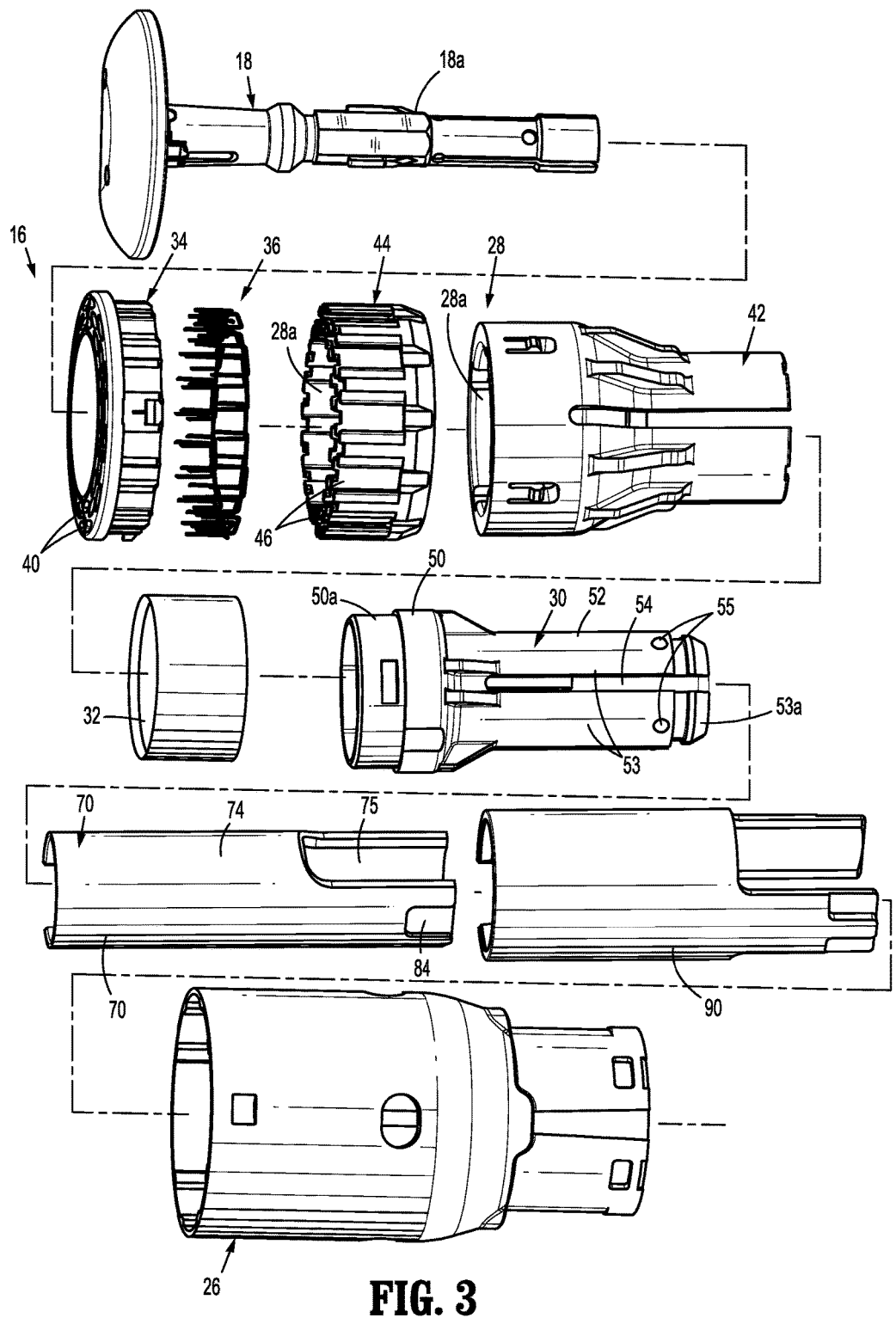
FIG. 3 is a side perspective view with parts separated of a distal portion of presently disclosed stapling device including the reload assembly and anvil assembly shown in FIG. 2.

Referring to FIGS. 2-3, the reload assembly 16 includes a housing 26, a pusher assembly 28, a knife carrier 30, an annular knife 32 supported on the knife carrier 30, a staple cartridge 34, and staples 36 supported within the staple cartridge 34. The staple cartridge 34 is annular and defines annular rows of staple pockets 40 (FIG. 3). Each of the staple pockets 40 supports one of the staples 36. The pusher assembly 28 includes an annular pusher 42 and a staple pushing member 44 that together define a longitudinal through bore 28a. The pusher 42 has a distal portion that abuts a proximal portion of the staple pushing member 44 such that distal movement of the pusher 42 within the housing 26 effects distal movement of the staple pushing member 44 within the housing 26. The staple pushing member 44 of the reload 16 has a plurality of fingers 46. Each of the plurality of fingers 46 is received within a respective one of the staple pockets 40 of the staple cartridge 34 and is movable through the respective staple pocket 40 to eject the staple 36 from the staple pocket 40 when the staple pushing member 44 is moved distally within the housing 26 from a retracted position to an advanced position.

Figure 4:
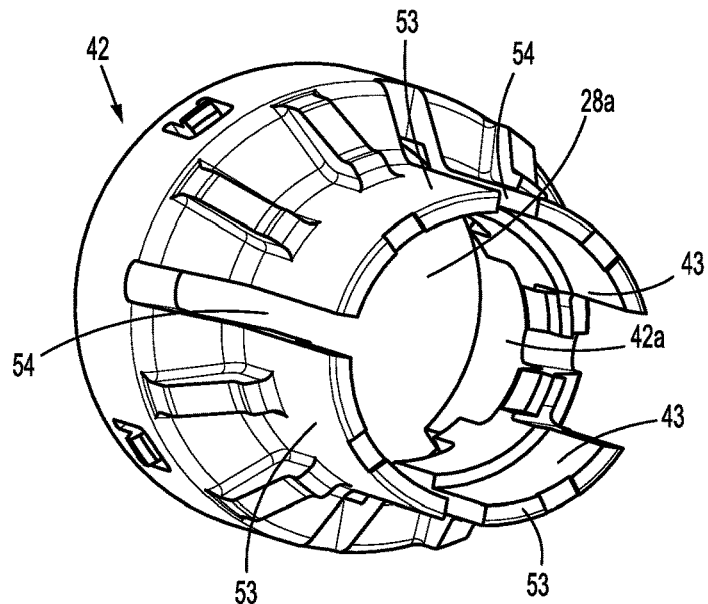
FIG. 4 is a side perspective view from a proximal end of an annular pusher of a pusher assembly of the reload assembly shown in FIG. 3.

Referring also to FIG. 4, the pusher 42 of the pusher assembly 28 includes an inner surface 42a that defines a portion of the longitudinal through bore 28a. The inner surface 42a of the pusher 42 is stepped outwardly at its proximal portion to further define counter bore 43 which is discussed in further detail below.

Referring again to FIG. 3, the anvil assembly 18 includes an anvil shaft 18a that is releasably coupled to an approximation mechanism (not shown) of the surgical stapling device 10 as is known in the art. The anvil shaft 18a is movable within a through bore 41 (FIG. 6) defined by an inner housing portion 26a of the housing 26 as the anvil assembly 18 moves between the spaced and approximated positions in relation to the staple cartridge 34.

Figure 4A:
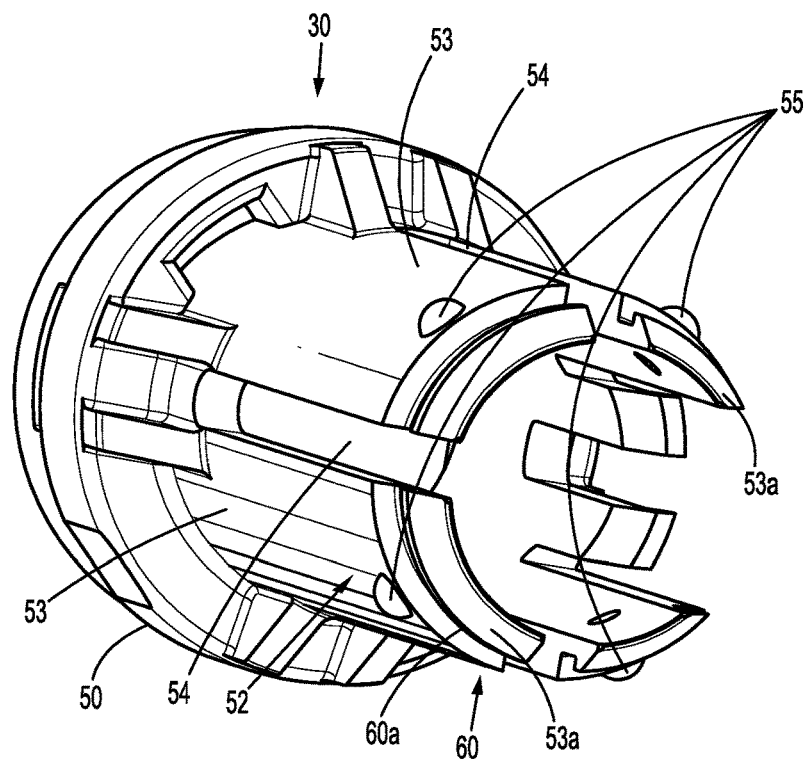
FIG. 4A is a side perspective view from a proximal portion of a knife carrier of the reload assembly shown in FIG. 3.

Referring to FIGS. 3 and 4A, the knife carrier 30 is movably supported within the through bore 28a of the pusher assembly 28 between retracted and advanced positions. In the advanced position of the knife carrier 30 (FIG. 7), the knife 30 extends from a distal end of the staple cartridge 32 and in the retracted position of the knife carrier 30 (FIG. 6), the knife 32 is recessed within the staple cartridge 34 to shield the knife 32 from contact by a clinician. The knife carrier 30 includes a substantially cylindrical distal portion 50 and a substantially cylindrical smaller diameter proximal portion 52. The smaller diameter proximal portion 52 is defined by a plurality of spaced resilient legs 53 that define slots 54 there between. The slots 54 receive projections (not shown) defined within the pusher 42 to guide movement of the knife carrier 30 from the retracted position to the advanced position within the pusher assembly 28. The longitudinal slots 54 also facilitate inward flexing of the resilient legs 53 of the knife carrier 30 from a first position in which the resilient legs 53 are engaged with a knife carrier pusher 70 (FIG. 5) (described in detail below) and a second position in which the knife carrier 30 is disengaged from the knife carrier pusher 70 (FIG. 8) as discussed in further detail below. In embodiments, the knife 32 is secured about the distal portion 50 of the knife carrier 30 such as by crimping. Alternately, other fastening techniques can be used to secure the knife 32 to the knife carrier 30. A distal-most portion 50a of the distal portion 50 of the knife carrier 30 can be recessed to receive the annular knife 32 such that the knife 32 and the knife carrier 30 define a smooth external surface.

Figure 5:
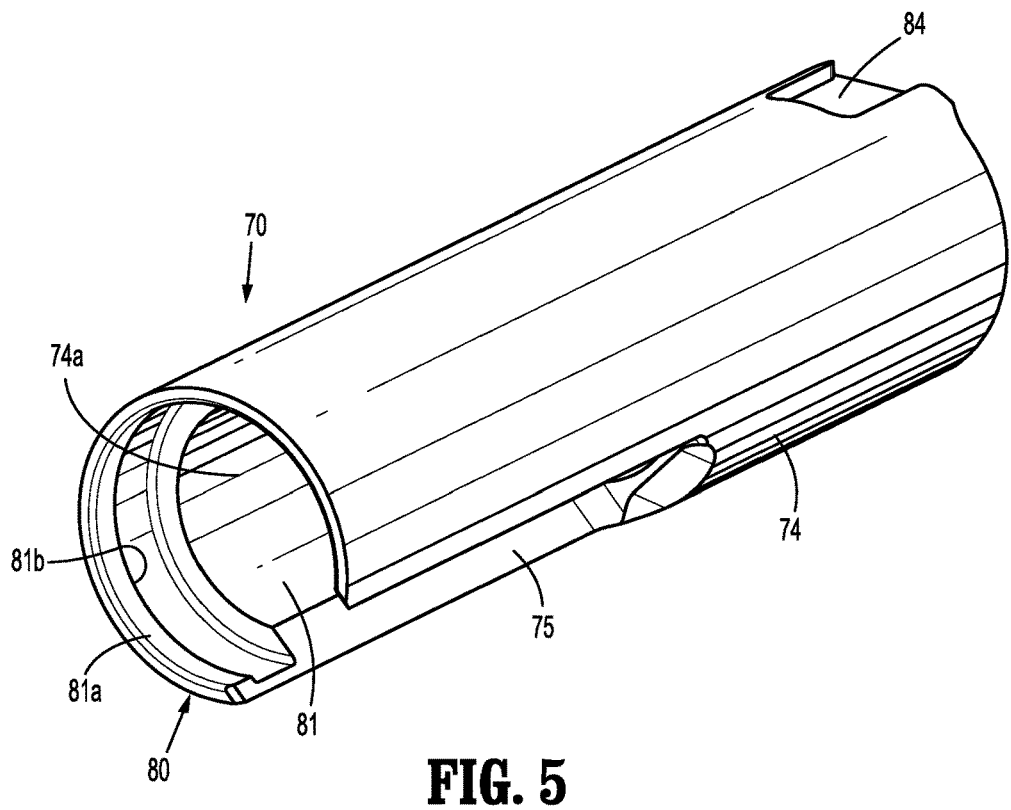
FIG. 5 is a side perspective view from a distal portion of a knife carrier pusher of the distal portion of the stapling device shown in FIG. 3.

Each of the resilient legs 53 of the knife carrier 30 supports an outwardly extending detent 55. The detents 55 can be integrally formed with the respective legs 53 or, alternatively, can be formed as a separate plug 55a (FIG. 6B) that is inserted into an opening 57 formed in a respective resilient leg 53. The detents 55 are positioned within the counter bore 43 (FIG. 6) of the pusher assembly 28 when the surgical stapling device 10 is in a pre-fired state with the knife carrier 30 and the pusher assembly 28 in retracted positions. Referring also to FIG. 4A, each of the resilient legs 53 of the knife carrier 30 defines a longitudinal axis and includes first engagement structure 60 that is configured to engage a distal portion of the knife carrier pusher 70 of the elongate body 14 as described in detail below to releasably couple the knife carrier 30 to the knife carrier pusher 70 (FIG. 5). In embodiments, the first engagement structure 60 includes an annular channel or recess 60a that is configured to receive second engagement structure 80 (FIG. 5) formed on a distal portion of the knife carrier pusher 70 as described in further detail below. Although shown as annular, other recess configurations are envisioned. The annular channel 60a of the first engagement structure 60 is defined by distal and proximal walls, wherein the proximal wall 80a is substantially orthogonal in relation to the longitudinal axis of the knife carrier 30. In embodiments, a proximal portion 53a of each resilient leg 53 of the knife carrier 30 is tapered inwardly towards the longitudinal axis of the knife carrier 30 in a proximal direction. The tapered proximal portion 53a and the longitudinal slots 54 of the knife carrier 30 facilitate attachment of the knife carrier 30 to the distal portion of the knife carrier pusher 70 as the reload assembly 16 is being attached to the elongate body 14 as described in detail below.

Referring also to FIG. 5, the knife carrier pusher 70 includes a substantially cylindrical body 74 having a cutout 75 that extends from a central portion of the body 74 to the distal portion of the body 74. The knife carrier pusher 70 is tubular and includes an inner wall 81 defining a through bore 74a. In embodiments, the second engagement structure 80 includes a protrusion 81a formed on a distal portion of the inner wall 81 of the knife carrier pusher 70. Although the protrusion 81a is shown as being annular, other configurations are envisioned. The annular protrusion 81a includes a proximal surface 81b that is substantially orthogonal to a longitudinal axis of the knife carrier pusher 70. The annular protrusion 81a is received within the annular channel 60a (FIG. 4A) of the knife carrier 30 when the resilient legs 53 are in the first position (FIG. 6) to couple the knife carrier 30 to the knife carrier pusher 70. The proximal wall 81b of the annular protrusion 81a is positioned to engage the proximal wall 80a (FIG. 6A) defining the annular channel 60a such that retraction of the knife carrier pusher 70 effects retraction of the knife carrier 30. In embodiments, the cylindrical body 74 of the knife carrier pusher 70 defines recesses 84 that are configured to engage a drive member (not shown) supported within the elongate body 14. The drive member is secured to the proximal portion of the knife carrier pusher 70 and is operable to advance and retract the knife carrier pusher 70 within the housing 26 of the reload assembly 16 as known in the art. U.S. Publication No. 2016/0106406 ("the '406 Publication") which was filed on Oct. 6, 2015 discloses such an elongate body or adaptor and is incorporated herein in its entirety by reference.

Figure 5A:
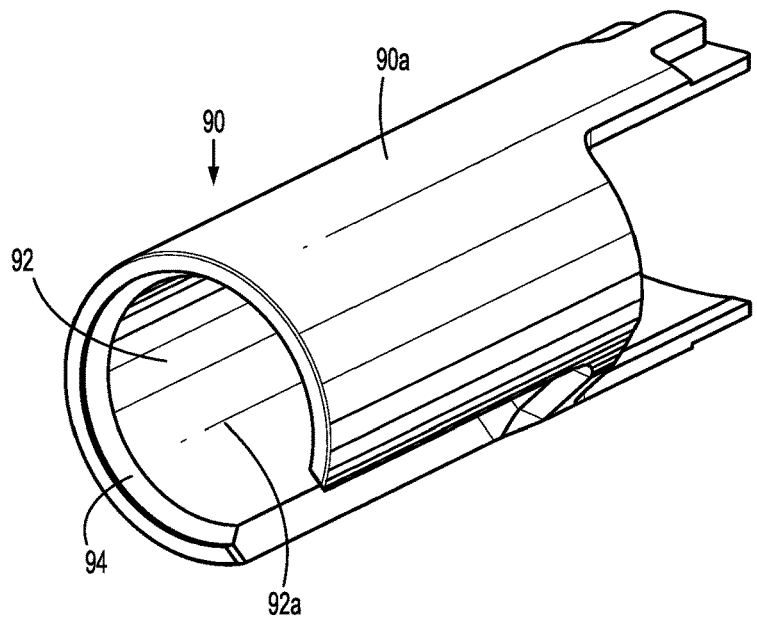
FIG. 5A is a side perspective view of a pusher drive member of the distal portion of the stapling device shown in FIG. 3.

Referring to FIGS. 3 and 5A, the elongate body 14 includes a pusher drive member 90 defining a longitudinal axis and having a tubular body 90a having an inner surface 92 defining a through bore 92a. A distal portion of the inner surface 92 defines a leading edge 94 that is tapered outwardly in a distal direction. The through bore 92a receives the knife carrier 30 and the knife carrier pusher 70 as the knife carrier 30 and the knife carrier pusher 70 are moved between retracted and advanced positions as described in further detail below. The tubular body 90a includes a proximal portion that is configured to engage structure within the elongate body 14 to effect translation of the pusher drive member 90 between the advanced and retracted positions. The '406 Publication which is incorporated herein in its entirety by reference discloses an elongate body including such structure.

FIGS. 6 and 6A illustrate a distal portion of the stapling device 10 in a pre-fired state. In the pre-fired state, the pusher assembly 28 and the knife carrier 30 of the reload 16 and the knife carrier pusher 70 and the pusher drive member 90 of the elongate body 14 are in retracted positions. In their retracted positions, the pusher assembly 28 and the pusher drive member 90 extend about an interface 106 between the first engagement structure 60 on the proximal portion of the resilient legs 53 of the knife carrier 30 and the second engagement structure 80 positioned on the distal portion the knife carrier pusher 70. In addition, the resilient legs 53 of the knife carrier 30 are in their first position with the detents 55 received within the counter bore 43 of the pusher 42 of the pusher assembly 28, and the knife carrier 30 and the knife carrier pusher 70 are in an engaged state.

Figure 6B:
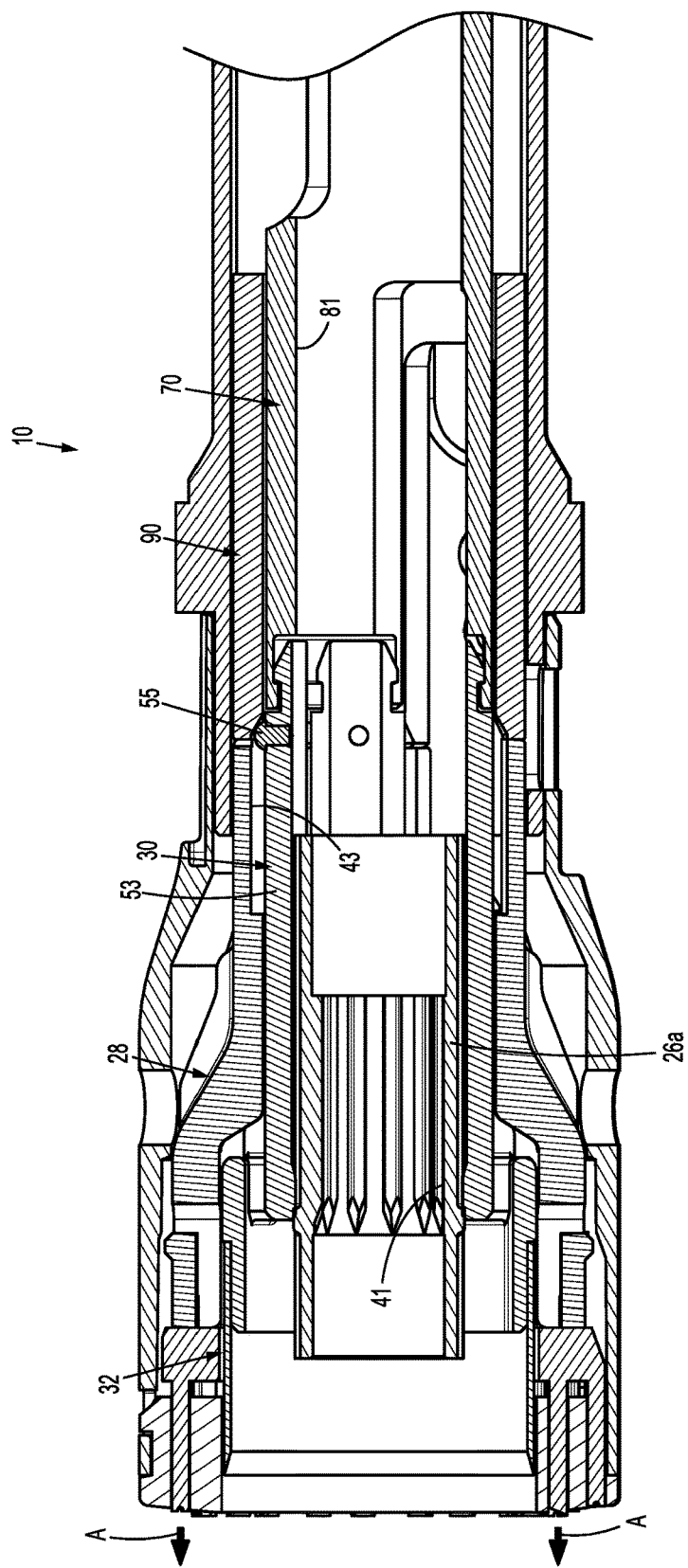
FIG. 6B is a side cross-sectional view of the distal portion of the surgical stapling device shown in FIG. 6 in a post-fired state with the knife carrier and knife carrier pusher in a retracted position.

FIG. 6B illustrates the distal portion of the surgical stapling device 10 in a post-fired state with the pusher assembly 28 and the pusher drive member 90 moved in the direction indicated by arrows "A" to their advanced positions to eject the staples 36 (FIG. 6) from the staple cartridge 34. In addition, the knife carrier 30, the knife 32, and the knife carrier pusher 70 remain in their retracted positions. In this state, the detents 55 are positioned in a proximal portion of the counter bore 43 such that the resilient legs 53 of the knife carrier 30 remain in their first position and the knife carrier 30 remains in engagement with the knife carrier pusher 70.

Figure 7:
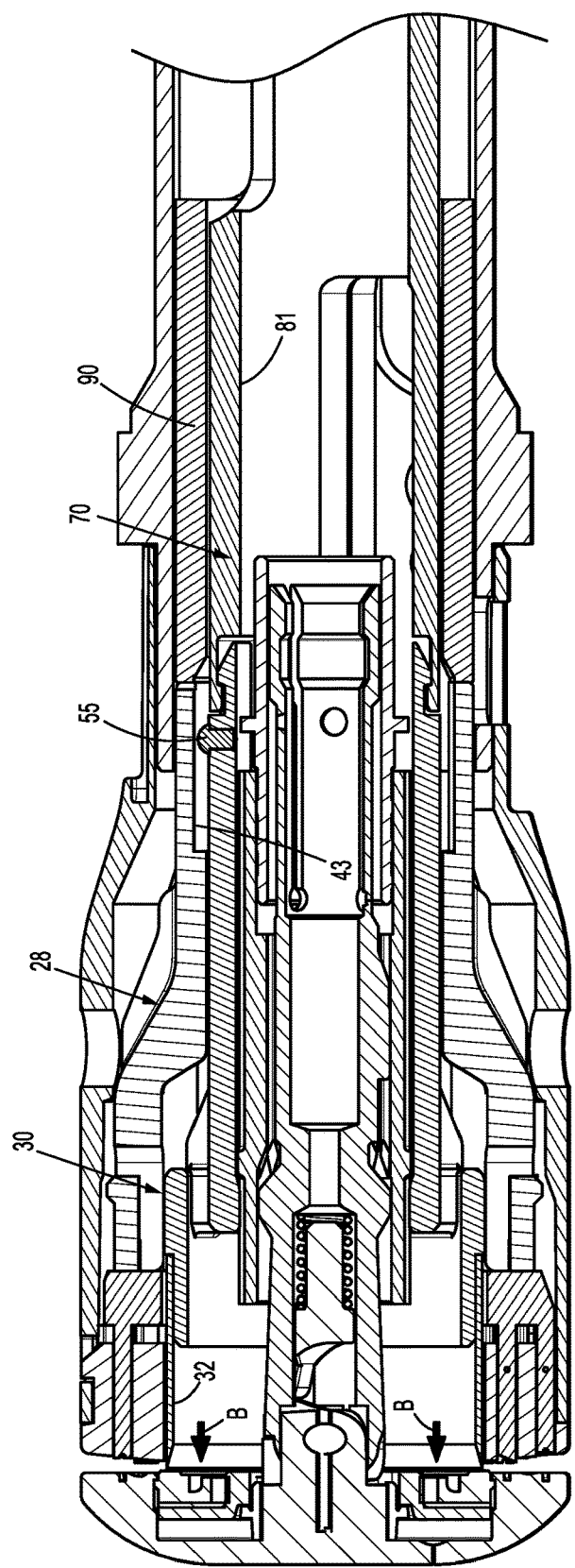
FIG. 7 is a side cross-sectional view of the distal portion of the surgical stapling device shown in FIG. 6A in a post-fired state with the knife carrier and knife carrier pusher in an advanced position.

FIG. 7 illustrates the distal portion of the surgical stapling device 10 in a post-fired state after the knife carrier pusher 70 and the knife 32 have been moved to their advanced positions in the direction indicated by arrows "B". In this state, the pusher assembly 28, pusher drive member 90, knife carrier 30 and knife carrier pusher 70 are in their advanced positions with the detents 55 in a central portion of the counter bore 43. As such, the resilient legs 53 of the knife carrier 30 remain in their first position with the first and second engagement structures 60, 80 of the knife carrier 30 and the knife carrier pusher 70 in engagement such that the knife carrier 30 remains coupled to the knife carrier pusher 70.

Figure 8:
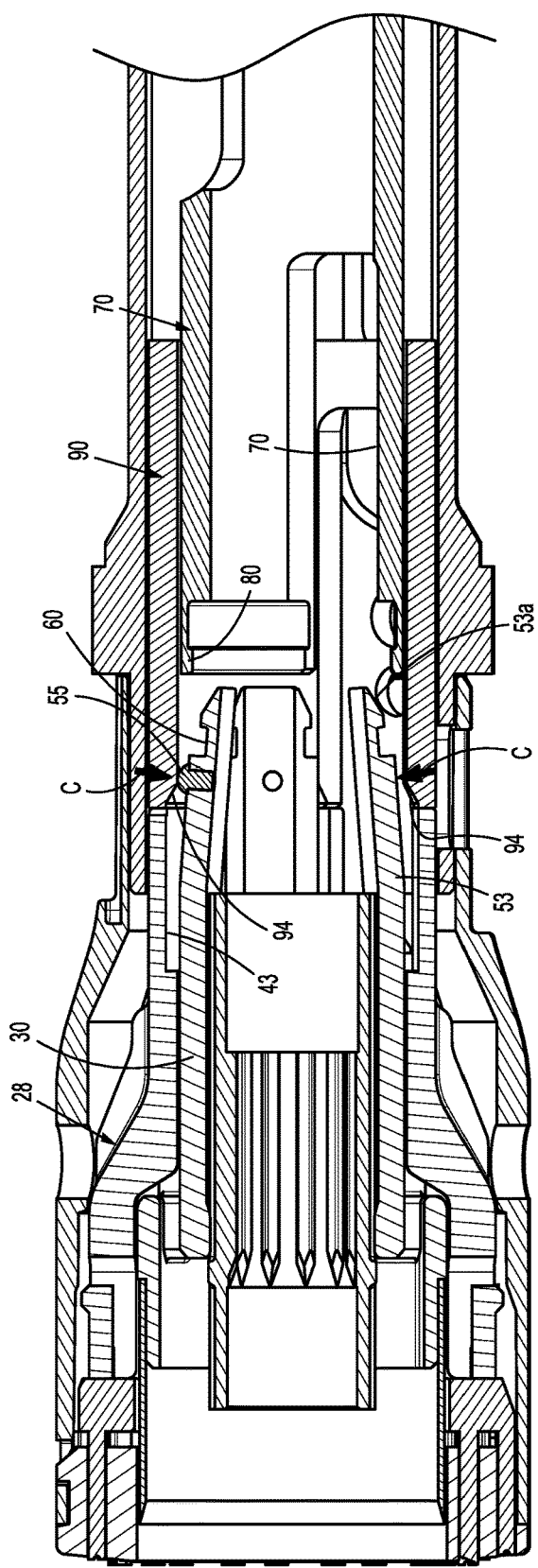
FIG. 8 is a side cross-sectional view of the distal portion of the surgical stapling device shown in FIG. 7 in a post-fired state with the knife carrier and the drive member in retracted positions, and the knife carrier pusher moving towards its retracted position to facilitate separation of the knife carrier and the knife carrier pusher.

Referring to FIG. 8, after the staples 36 (FIG. 3) have been fired and tissue has been cut, the pusher drive member 90 is retracted. As discussed above, the pusher drive member 90 is in abutting relation with the pusher assembly 28 and thus, the pusher assembly 28 does not retract with the pusher drive member 90. Subsequently (or simultaneously), the knife carrier pusher 70 is moved to a fully retracted position to retract the knife carrier 30 within the pusher assembly 28 and the pusher drive member 90. As the knife carrier pusher 70 is moved to the fully retracted position, the proximal wall 81b of the annular protrusion 81a of the second engagement structure 80 engages the proximal wall 80a defining the annular channel 60a such that retraction of the knife carrier pusher 70 effects retraction of the knife carrier 30. Because the walls 80a and 81b are substantially orthogonal to the longitudinal axis of the knife carrier 30 as discussed above, the force applied by the wall 81b onto the wall 80a does not urge the resilient legs 53 towards their second position.

As the knife carrier 30 is moved towards its retracted position, the detents 55 move through the counter bore 43 such that the resilient legs 53 remain in their first position engaged with the knife carrier pusher 70 to retract the knife 32 into the housing 26 of the reload assembly 16. After the knife 32 is retracted into the housing 26, the detents 55 are positioned to engage the tapered leading edge 94 of the pusher drive member 90. When the detents 55 engage the tapered leading edge 94 of the pusher drive member 90, the resilient legs 53 are urged inwardly in the direction indicated by arrows "C" from their first position towards their second position to disengage the first engagement structure 60 from the second engagement structure 80 and uncouple the knife carrier 30 from the knife carrier pusher 70. By providing detents 55, the present reload assembly 16 does not rely on a back angle on the knife carrier pusher 70 to effect uncoupling of the knife carrier 30 from the knife carrier pusher 70. The detents 55 function to accurately control the timing of separation between the knife carrier 30 and the knife carrier pusher 70 and minimize the likelihood of premature separation of the knife carrier 30 from the knife carrier pusher 70 while minimizing the force required to effect separation of the knife carrier 30 and the knife carrier pusher 70.

As discussed above, the proximal portion 53a of each resilient leg 53 of the knife carrier 30 is tapered inwardly towards the longitudinal axis of the knife carrier 30 in a proximal direction. Referring again to FIG. 6A, when the reload assembly 16 is attached to the distal portion of the elongate body 14 of the surgical stapling device 10, the tapered proximal portion 53a of the resilient legs 53 will engage a distal face 100 of the knife carrier pusher 70. Engagement between the tapered proximal portion 53a of the resilient legs 53 and the distal face 100 of the knife carrier pusher 70 will cam the resilient legs 53 downwardly to allow the first engagement structure 60 to pass by the second engagement structure 80. Due to the resilient nature of the legs 53, the second engagement structure 80 will snap into the first engagement structure 60 when the structures are aligned to couple the knife carrier 30 and the knife carrier pusher 70.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. For example, any of the embodiments disclosed herein could include staples with different sizes and/or surfaces with different heights on the staple cartridge and/or anvil. Any of the embodiments disclosed herein can include a surgical buttress that may or may not be used to deliver a therapeutic substance such as a drug or brachytherapy seed. As well, one skilled in the art will appreciate further features and advantages of the disclosure based on the above-described embodiments. Accordingly, the disclosure is not to be limited by what has been particularly shown and described, except as indicated by the appended claims.

What is claimed is:
1. A surgical stapling device comprising:
an elongate body defining a longitudinal axis and having a proximal portion and a distal portion, the elongate body including a pusher drive member and a knife carrier pusher, the pusher drive member having an inner surface defining a through bore having a tapered distal portion;
a reload assembly including a housing, a staple cartridge supporting a plurality of staples, a pusher assembly, a knife carrier, and a knife, the pusher assembly movably supported within the housing between a retracted position and an advanced position to eject the plurality of staples from the staple cartridge, the pusher assembly having an inner surface defining a through bore, the inner surface having a proximal portion defining a counter bore, wherein the knife carrier supports a knife and includes first engagement structure, the knife carrier having at least one detent; and the knife carrier pusher including second engagement structure configured to releasably engage the first engagement structure of the knife carrier to couple the knife carrier pusher to the knife carrier, the first engagement structure being movable from a first position engaged with the second engagement structure to a second position disengaged from the second engagement structure;

wherein when the surgical stapling device is in a pre-fired state, the at least one detent is positioned within the counter bore of the pusher assembly, and when the knife carrier is retracted after the surgical stapling device has been actuated to eject the plurality of staples and to dissect tissue, the detents are positioned to engage the tapered distal portion of the pusher drive member to urge the first engagement from the first position towards the second position to uncouple the knife carrier from the knife carrier pusher.

2. The surgical stapling device of claim 1, wherein the knife carrier includes a proximal portion defined by a plurality of flexible legs.

3. The surgical stapling device of claim 2, wherein the at least one detent includes a detent supported on each of the plurality of flexible legs.

4. The surgical stapling device of claim 3, wherein each of the detents extends outwardly from a longitudinal axis of the knife carrier.

5. The surgical stapling device of claim 3, wherein each of the detents is integrally formed with a respective one of the plurality of flexible legs.

6. The surgical stapling device of claim 5, wherein the first engagement structure is formed on a proximal portion of the plurality of flexible legs.

7. The surgical stapling device of claim 6, wherein the first engagement structure includes a recess formed on the proximal portion of the plurality of flexible legs.

8. The surgical stapling device of claim 7, wherein the recess includes an annular channel.

9. The surgical stapling device of claim 7, wherein the proximal portion of each of the plurality of flexible legs is tapered towards a longitudinal axis of the knife carrier in the proximal direction.

10. The surgical stapling device of claim 9, wherein the protrusion is annular.

11. The surgical stapling device of claim 7, wherein the second engagement structure includes a protrusion configured to be received within the recess of the first engagement structure.

12. The surgical stapling device of claim 11, wherein the recess of the first engagement structure is defined by a proximal wall that is orthogonal in relation to the longitudinal axis of the knife carrier.

13. The surgical stapling device of claim 12, wherein the protrusion of the second engagement structure is defined by a proximal wall which is orthogonal in relation to the longitudinal axis of the knife carrier pusher.

14. The surgical stapling device of claim 12, wherein the proximal wall of the second engagement structure is positioned to engage the proximal wall of the first engagement structure to translate proximal movement of the knife carrier pusher into proximal movement of the knife carrier.

15. The surgical stapling device of claim 1, wherein the knife carrier is movably positioned within the through bore defined by the pusher assembly.

16. The surgical stapling device of claim 1, wherein the handle assembly is an electrically powered handle assembly.

17. The surgical stapling device of claim 1, wherein the reload assembly is releasably coupled to the elongate body.

18. The surgical stapling device of claim 17, wherein the annular pusher is positioned to abut a proximal portion of the staple pushing member.

19. The surgical stapling device of claim 1, wherein the pusher assembly includes an annular pusher and a staple pushing member.

* * * * *